United States Patent [19]

Redden et al.

[11] 4,263,934
[45] Apr. 28, 1981

[54] DENTAL WASTE TRAP

[76] Inventors: Lynn M. Redden, P.O. Box 1535, Cave Creek, Ariz. 85331; John Schmidt, 2517 N. 67th Cir., Phoenix, Ariz. 85035

[21] Appl. No.: 113,650

[22] Filed: Jan. 21, 1980

[51] Int. Cl.³ .................................... F16L 43/00
[52] U.S. Cl. ........................ 137/140; 137/247.39; 433/92; 220/82 R; 220/404
[58] Field of Search ............ 137/140, 203, 247.35, 137/247.39; 220/82 R, 404; 4/263; 210/532 R, 247; 433/92

[56] References Cited

U.S. PATENT DOCUMENTS

| 2,467,547 | 4/1949 | Birnbaum | 210/532 R |
| 3,285,461 | 11/1966 | Santelli | 220/404 |
| 3,776,408 | 12/1973 | Wald | 220/404 X |
| 4,151,929 | 5/1979 | Sapien | 220/404 |
| 4,213,536 | 7/1980 | Hafner | 220/82 R |

FOREIGN PATENT DOCUMENTS 849695  9/1960  United Kingdom ............... 137/247.35

Primary Examiner—Harold W. Weakley
Attorney, Agent, or Firm—Gregory J. Nelson

[57] ABSTRACT

A waste trap for collecting solid wastes in a drain system connectable at a fitting to a drain pipe. The trap includes a removable receptacle which is disposable or houses a disposable insert when the trap is full. A siphon is associated with the trap to draw down the liquid level to facilitate removal of the receptacle.

5 Claims, 5 Drawing Figures

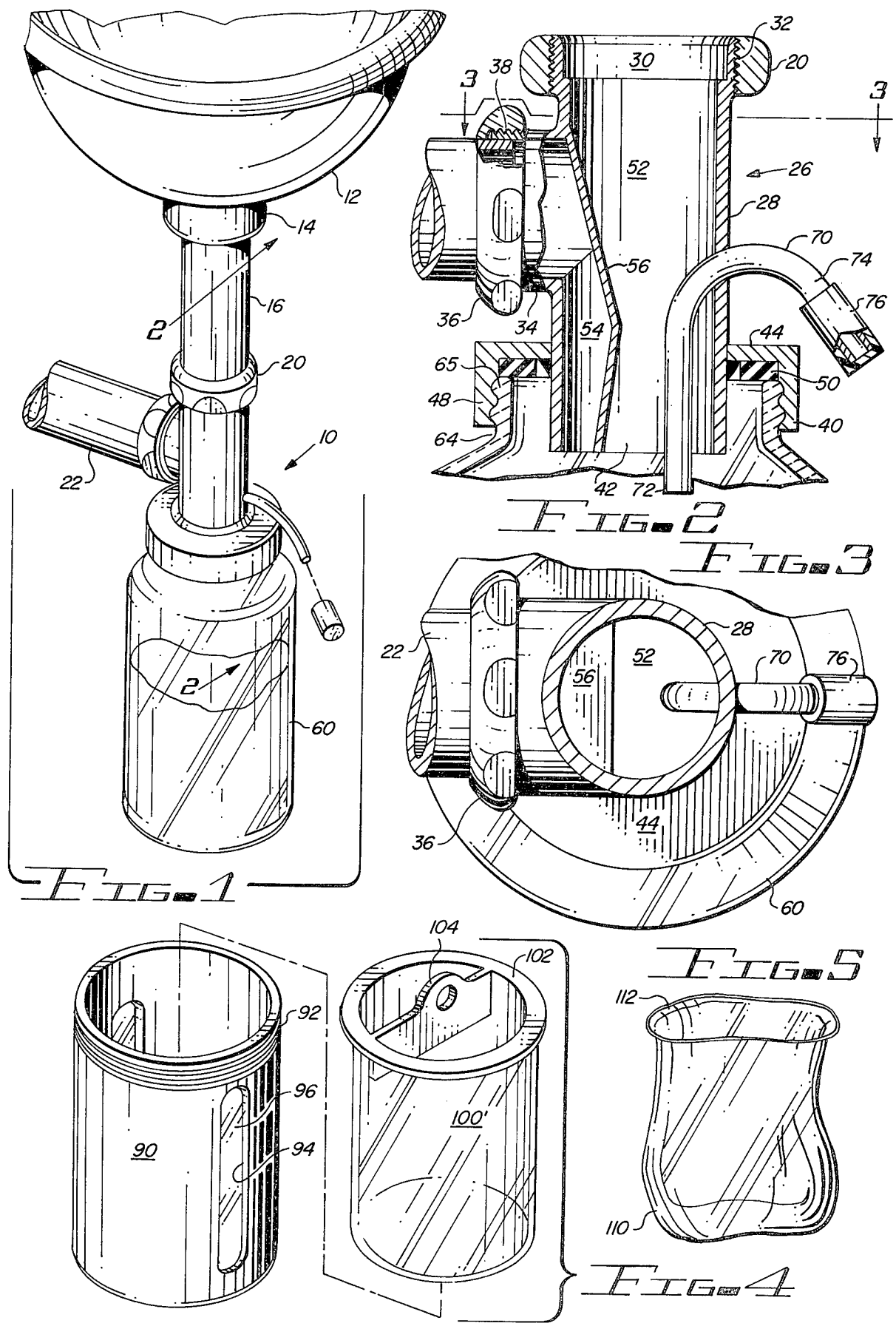

DENTAL WASTE TRAP

The present invention relates to a waste trap. More particularly, the present invention relates to a waste trap for collection of solid waste particles of the type often discharged with liquid waste in dental and medical laboratories.

In the manufacture and processing of dental prosthetic devices, waste solid materials such as plaster and plastic particles are discharged as waste into a basin or sink and then flushed to a waste disposal system. These solid particles may be fine particles such as pieces of plaster and like materials used in manufacturing dental appliances and devices. The normal drain trap connected to most conventional sinks is a "P" trap which has a U or loop section interposed between the drain tailpipe and the horizontal pipe leading to the drain system. Solid particles of waste material collect in this section and in the event the drain becomes clogged, the section must be removed and cleaned. This conventional "P" trap is not generally acceptable for use in environments such as dental laboratories. The particulate matter such as particles of plastic and plaster will quickly clog the conventional trap as a solidified mass making it difficult if not impossible to clean the trap. Further, even if cleaning is possible, the procedure involved in removing the trap, cleaning it and replacing it is unduly difficult, unsanitary and time consuming.

Accordingly, there exists a need for an improved drain trap for the collection of solid waste particles discharged from dental, medical and similar laboratory environments. Several traps for waste pipes can be found in the prior art which provide a collection chamber for particles and which facilitate cleaning. U.S. Pat. No. 1,345,549, shows a dental appliance in the nature of a trap to be connected with the customary fountain at the dentist chair to collect any particles of gold and silver which may be discharged into the fountain. Similarly, Waibel, U.S. Pat. No. 904,286, shows a waste trap having a container or receiver which is easily removable. However, these prior traps do not lend themselves to use in dental laboratory situations and further inherently involve the removal, cleaning and replacement of the collection container.

Briefly, the present invention provides an improved dental waste trap which is connectable to most conventional drain systems. The waste trap includes a fitting connectable to the drain or tailpipe and waste pipe of the drain at a nut and gasket. The fitting defines an inlet and an outlet section which are separated by a baffle. A mechanical fastener such as a threaded collar is carried on the fitting to receive a collection receptacle. Preferably the collection receptacle is transparent glass or plastic and is disposable once the receptacle has accumulated a quantity of solid material. A siphon extends through the fitting into the collection receptacle and may be activated to draw the liquid level in the receptacle below the collar to facilitate removal of the receptacle.

In alternate embodiments, the receptacle houses a pliable or rigid liner which receives a solid material which is removable and is disposable. A new liner is replaced within the receptacle at the time of cleaning.

The above and other objects in advantage of the present invention will become more apparent from the following specification, claims and drawings in which:

FIG. 1 is a perspective view illustrating the waste trap of the present invention installed in a waste system;

FIG. 2 is a sectional view taken along lines 2—2 of FIG. 1;

FIG. 3 is a sectional view taken along lines 3—3 of FIG. 2;

FIG. 4 is an exploded view illustrating another form of the receptacle as a component of the waste trap of the present invention; and FIG. 5 illustrates still another form of liner usable with the receptacle as shown in FIG. 4.

Turning now to the drawings, the waste trap of the present invention is generally designated by the numeral 10 and is shown installed in a drain system connected to sink 12. Sink 12 may be of any type that has an outlet or opening 14 from which vertically extends a conduit or tail piece 16 which is connected to waste trap 10 at coupling 20. The drain discharge pipe 22 carries effluent to the main drain or sewer system.

As best seen in FIG. 2, the waste trap 10 includes a fitting 26 generally in the form of a tee having a cylindrical body section 28. One end of the body 28 defines an inlet 30 having conventional threads 32 connectable to the tailpipe 16 at nut 20 as has been explained. A suitable sealing member or gasket can be interposed between the tailpipe and the inlet 30 to seal the connection. A discharge section 34 extends perpendicularly from body 28 and is connectable to drain pipe 22 at connector or nut 36. Discharge section 34 is provided with threads 38 for reception of coupling or nut 36.

Collar 40 is secured to the body 28 of fitting 26 adjacent the lower end 42. Collar 40 has a horizontal top 44 and a generally annular depending lower flange 46 having an interiorly threaded section 48. An appropriate seal 50 may be provided at the interior of top or cap section 44. Collar 40 is adapted for a detachable securement of a container or receptacle as will hereinafter be explained.

Fitting 26 is, as best seen in FIG. 2, is partitioned having an inlet channel 52 and an outlet channel 54 by baffle 56 extending generally longitudinally across the interior wall within the fitting from the juncture with section 34. Channel 52 extends from adjacent the inlet end 30 to the lower end at a location below collar 40. Channel 54 extends from lower end 42 communicating with outlet section 34.

Container 60, preferably of transparent material such as glass or plastic, is shown as being generally cylindrical having a neck 64 provided with threads 65 cooperable with threaded section 48 of collar 40. Container 60 is detachably secured to collar 40 at the cooperable threaded sections 48 and 65.

A generally U-shaped siphon tube 70 extends through the wall of 48 of fitting 26 depending to a location below end 42 of the fitting. The opposite end 74 of the siphon tube 70 is located adjacent collar 40 and is provided with a removable cap 76.

A more complete understanding of the present invention will be had from the following description of installation and use. The waste trap 10 is installed in the drain system as shown in FIG. 1. The upper end of fitting 26 is secured to the drain conduit or tail piece 16 at connector or nut 20. The discharge or outlet fitting 34 is connected to drain pipe 22 at connector or nut 36. Container 60 is secured to collar 40. Cap 76 is positioned in place on siphon tube 70. A stream of water discharged from the outlet 14 of the sink is directed through channel 52 into the subjacent container 60. The heavier particles and other sedimentation will settle to the bottom of container 60. The liquid will discharge to the waste pipe 22 via channel 54. The normal liquid level remains at approximately line 80 as shown in FIG. 3 to form a hydraulic seal between the channels 52 and 54 to prevent gases and obnoxious odors from entering through the drain system and sink.

At such time as container 60 is substantially full of waste materials which have settled within the container, siphon cap 70 is removed and a siphon action initiated. This causes the liquid within the fitting and the upper end of the container to be discharged. The liquid can be discharged into any convenient container. Once the water level is drawn down below the upper edge of neck 48 of the container, container 60 can be simply removed by twisting the container to remove the container from collar 40 at the threaded section. Container 60 can either be emptied or cleaned or preferably, for convenience and sanitary reasons, discarded and replaced with a new container. The procedure is simple and requires a minimum of time for the attendant to accomplish the removal and replacement of a new container.

FIG. 4 illustrates an alternate embodiment of the present invention which the outer container 90 is shown as a generally cylindrical rigid member having threaded section 9 at the upper end for engagement with collar 40. A longitudinally extending slot 94 is provided with a transparent window 96 so the contents of the container 90 are clearly visible. Container 90 may be fabricated from any convenient materials such as metal or a rigid plastic such as PVC or the like. An insert or liner 100, also shown as being generally cylindrical, is dimensioned to be insertable within container 90. An upper flange 102 extends around the open end of receptacle 100. Preferably a diametrically extending bail 104 is provided to facilitate insertion and removal of the receptacle 100 within container 90. Receptacle 100 is preferably of a transparent or translucent material so the contents of the receptacle 100 are visible through window 94 in container 90.

When a predetermined quantity of waste materials has collected in the lower settling portion of insert 100, the liquid level is lowered by siphon 70 as described above. Receptacle 90 is removed from collar 40 and the liner 100 removed and cleaned and replaced or a new insert is positioned within the outer container 90.

FIG. 4 shows an alternate embodiment for the liner designated by the numeral 110. Liner or insert 110 is a form of a flexible, liquid impervious receptacle which is insertable within container 90. The upper edge of receptacle 110 is preferably flared at edge 112 so this edge may be interposed between the upper edge of the container 90 and seal 52 provide a tight liquid seal. When the receptacle 110 has accumulated a predetermined quantity of solids, the container 90 can be removed from collar 40 and receptacle 110 and the contents discarded.

Thus it will be seen from the foregoing that the present invention provides a simple and effective waste trap for drain systems in which a quantity of solid or particulate matter are discharged along with the liquid. The drain system is easy to install and periodic removal of solid particles is easily accomplished in a sanitary manner.

It will be obvious to those skilled in the art to make various changes, alterations and modifications to the invention described herein. To the extent that these changes, alterations and modifications do not depart from the spirit and scope of the appended claims, they are intended to be encompassed therein.

We claim:

1. A waste trap for collecting sediment in a drain system having an outlet and a drain pipe and adapted to be interposed therebetween comprising:
   (a) fitting having a body defining an interior, said body having an inlet connectable to said drain and a discharge end, baffle means extending in said interior defining a first flow passage extending from said inlet to said discharge end, and a second flow passage extending from said discharge end to said outlet;
   (b) collar means associated with said fitting for detachably securing a container thereto;
   (c) container means detachably securable at said collar for receiving and collecting sediment therein; and
   (d) siphon means for selectively withdrawing liquid from said waste trap.

2. The waste trap of claim 1 wherein said container is transparent.

3. The waste trap of claim 1 wherein said container includes an outer generally rigid member and a removable inner liner.

4. The waste trap of claim 3 wherein said outer rigid member is provided with means for viewing said inner liner.

5. The waste trap of claim 3 wherein said inner liner is a flexible bag.

* * * * *